United States Patent
Peter et al.

(10) Patent No.: US 9,545,648 B2
(45) Date of Patent: Jan. 17, 2017

(54) MAGNETIC PARTICLE WASHING APPARATUS AND METHOD

(71) Applicant: Siemens Healthcare Diagnostics Inc., Tarrytown, NY (US)

(72) Inventors: Moses Peter, Bridgeport, CT (US); Michael Avdenko, Rochester, NY (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 91 days.

(21) Appl. No.: 14/404,231

(22) PCT Filed: May 21, 2013

(86) PCT No.: PCT/US2013/041945
§ 371 (c)(1),
(2) Date: Nov. 26, 2014

(87) PCT Pub. No.: WO2013/181019
PCT Pub. Date: Dec. 5, 2013

(65) Prior Publication Data
US 2015/0165491 A1   Jun. 18, 2015

Related U.S. Application Data

(60) Provisional application No. 61/653,573, filed on May 31, 2012.

(51) Int. Cl.
*B08B 5/04* (2006.01)
*B08B 3/10* (2006.01)
(Continued)

(52) U.S. Cl.
CPC ............... *B08B 3/102* (2013.01); *B01L 99/00* (2013.01); *G01N 33/54393* (2013.01);
(Continued)

(58) Field of Classification Search
None
See application file for complete search history.

(56) References Cited

U.S. PATENT DOCUMENTS 5,741,708 A    4/1998  Carey et al.
2005/0196867 A1   9/2005  Bower et al.
(Continued)

FOREIGN PATENT DOCUMENTS

EP   2 031 404 A2    3/2009
WO   91/16979 A2   11/1991
WO   WO 9116979 A2 *  11/1991

OTHER PUBLICATIONS

Extended EP Search Report dated Jan. 25, 2016 of corresponding European Application No. 137962627, 4 Pages.
(Continued)

*Primary Examiner* — Eric Golightly (57) ABSTRACT

Methods and apparatus are adapted to wash magnetic particles isolated in a vessel. The methods include providing a vessel with wash liquid and a layer of magnetic particles, providing a probe having aspiration capability, positioning a probe tip above the layer of magnetic particles, aspirating at least some of the wash liquid above the layer, positioning the probe tip below the layer, and aspirating at least some of the wash liquid from below the layer of magnetic particles. The suction may be turned off as the probe tip descends past the layer. A novel magnetic particle washing apparatus are disclosed.

13 Claims, 4 Drawing Sheets

(51) Int. Cl.
*G01N 35/00* (2006.01)
*B01L 99/00* (2010.01)
*G01N 33/543* (2006.01)

(52) U.S. Cl.
CPC .. *G01N 35/0098* (2013.01); *B01L 2200/0647* (2013.01); *G01N 2035/00564* (2013.01); *G01N 2446/00* (2013.01)

(56) References Cited

U.S. PATENT DOCUMENTS

| | | |
|---|---|---|
| 2005/0272049 A1 | 12/2005 | Banerjee et al. |
| 2007/0172390 A1 | 7/2007 | Ootani et al. |
| 2007/0212698 A1* | 9/2007 | Bendele ............... G01N 33/491 435/6.16 |
| 2009/0068062 A1 | 3/2009 | Jafari et al. |
| 2010/0227387 A1 | 9/2010 | Safar et al. |
| 2012/0034703 A1 | 2/2012 | Nguyen et al. |
| 2012/0061302 A1 | 3/2012 | Siddiqi |
| 2012/0071643 A1 | 3/2012 | Helfer et al. |

OTHER PUBLICATIONS

PCT International Search Report and Written Opinion dated Nov. 1, 2013 (12 Pages).

* cited by examiner

MAGNETIC PARTICLE WASHING APPARATUS AND METHOD

FIELD

The present invention relates generally to apparatus and methods adapted to wash magnetic particles used in diagnostic testing.

BACKGROUND

In medical testing and processing, the use of robotics may minimize exposure to, or contact with, bodily fluid samples (otherwise referred to as "specimens") and/or may significantly increase productivity. For example, in some automated testing and processing systems (e.g., clinical analyzers), a specimen and/or reagent liquid may be aspirated from one liquid-containing vessel (e.g., a sample collection tube or reagent container) and may be transferred to another liquid-containing vessel (e.g., a reaction cuvette).

Such liquid transfer may be accomplished by the use of a robot, which may include a suitable moveable robotic component, an aspirating and dispensing apparatus, and an attached probe. The probe may be moved in one or more coordinate directions by the robot. In this manner, the probe may aspirate a specimen or reagent liquid from a first liquid-containing vessel, and then move and dispense the specimen or reagent liquid into another liquid-containing vessel.

In some medical diagnostic testing, magnetic particles may be introduced into the liquid-containing vessel (e.g., a cuvette) and during a reaction, a chemical constituent or component of interest (e.g., an analyte) may bind to active surfaces of the magnetic particles. After the reaction, the magnetic particles may undergo an automated wash process. The wash process is intended to remove any remaining contaminated liquids and/or other contaminants and leave behind just the magnetic particles with the chemical constituent or component of interest bound thereto. Prior to the wash process, the magnetic particles may be drawn to a side of the liquid-containing vessel (e.g., a cuvette), such as by a magnet.

In existing wash processes, some magnetic particles may be inadvertently lost, thereby reducing an amount of the chemical constituent or component of interest remaining to test. Moreover, sometimes, foam, wash liquid and/or other liquid may inadvertently adhere to the walls of the liquid-containing vessel (e.g., a cuvette).

Accordingly, wash methods and apparatus that may improve a thoroughness of a washing of the magnetic particles are desired.

SUMMARY

In a first aspect, a method of washing magnetic particles is provided. The method includes providing a vessel with wash liquid and a layer of magnetic particles, providing a probe having aspiration capability, positioning a probe tip of the probe above the layer of magnetic particles, aspirating at least some of the wash liquid above the layer of magnetic particles, positioning the probe tip below the layer of magnetic particles, and aspirating at least some of the wash liquid from below the layer of magnetic particles.

According to another method aspect, a method of washing magnetic particles is provided. The method includes providing a probe having a probe tip and having suction capability, providing a vessel containing a wash liquid and a layer of magnetic particles wherein a top liquid portion of the wash liquid is above the layer of magnetic particles and a bottom liquid portion of the wash liquid is below the layer of magnetic particles, positioning the probe tip above the layer of magnetic particles and in the top liquid portion of the wash liquid, aspirating into the probe tip at least some of the top liquid portion of the wash liquid above the layer of magnetic particles while descending the probe tip at a descent rate of less than about 5 cm/s, positioning the probe tip below the layer of magnetic particles by passing the probe past the layer of magnetic particles with a suction to the probe tip turned off, and aspirating at least some of the bottom liquid portion of wash liquid from below the layer of magnetic particles while the probe is positioned at less than about 10 mm from a bottom of the vessel.

In an apparatus aspect, a magnetic particle washing apparatus is provided. The magnetic particle washing apparatus includes a robot, a probe coupled to the robot and having a probe tip, an aspirating and dispensing unit, a holder adapted to hold a vessel containing a wash liquid and a layer of magnetic particles, and a controller coupled to the robot and aspirating and dispensing unit, the controller operational to: position the probe tip above the layer of magnetic particles, aspirate at least some of the wash liquid from above the layer of magnetic particles, position the probe tip below the layer of magnetic particles, and aspirate at least some of the wash liquid from below the layer of magnetic particles.

Still other aspects, features, and advantages of the present invention may be readily apparent from the following detailed description by illustrating a number of example embodiments and implementations, including the best mode contemplated for carrying out the present invention. The present invention may also be capable of other and different embodiments, and its several details may be modified in various respects, all without departing from the scope of the present invention. Accordingly, the drawings and descriptions are to be regarded as illustrative in nature, and not as restrictive. The drawings are not necessarily drawn to scale. Moreover, like reference numerals are used herein to denote like elements. The invention is to cover all modifications, equivalents, and alternatives falling within the scope of the invention.

DETAILED DESCRIPTION

As described above, in certain chemical diagnostic testing, such as analysis of assays, immunoassays, and chemical analysis, magnetic particles having a high affinity surface may be used as a carrier for a chemical constituent or component of interest (e.g., an analyte). For example, in clinical analyzers, once the chemical constituent or component of interest (e.g., an analyte) is effectively bound to the magnetic particles, the magnetic particles may be separated using a magnetic field (via a magnet field generating device) into a defined band along a side of the vessel (e.g., cuvette). Once separated, it is intended that the remaining fluid, which may include liquid reagent, water, or other liquids, may be removed by aspirating with a probe.

The isolated and defined band of magnetic particles may then undergo one or more washing sequences. In current washing methods, however, removal of all the top foam and droplets of liquid adhering to the walls of the vessel (e.g., cuvette) is difficult. Moreover, sometimes magnetic particles are inadvertently removed as a part of the magnetic particle washing process. This is not desirable as portions of the chemical component or constituent of interest that is bound to the removed magnetic particles are also removed. Accordingly, washing methods are sought that are more effective at removing top foam and/or wall-adhered liquid droplets, while minimizing magnetic particle loss during the magnetic particle washing method.

In view of the foregoing problems, embodiments of the present invention provide, in one aspect, improved magnetic particle washing methods. In this first aspect, the washing method includes positioning a probe tip of a probe above a defined layer of magnetic particles covered in a wash liquid, aspirating at least some of the wash liquid above the layer of magnetic particles, moving the probe tip below the layer of magnetic particles, such as with the probe suction turned off, and aspirating at least some of the wash liquid from below the layer of magnetic particles.

The probe tip position, descent rate, and/or volume aspiration rate may be controlled for aspiration above and below the layer of magnetic particles. Accordingly, excellent top surface foam removal, top wash liquid portion removal, and bottom wash liquid portion removal may be achieved while minimizing magnetic particle loss.

These and other aspects and features of embodiments of the invention will be described with reference to FIGS. 1-9 herein.

Figure 1:
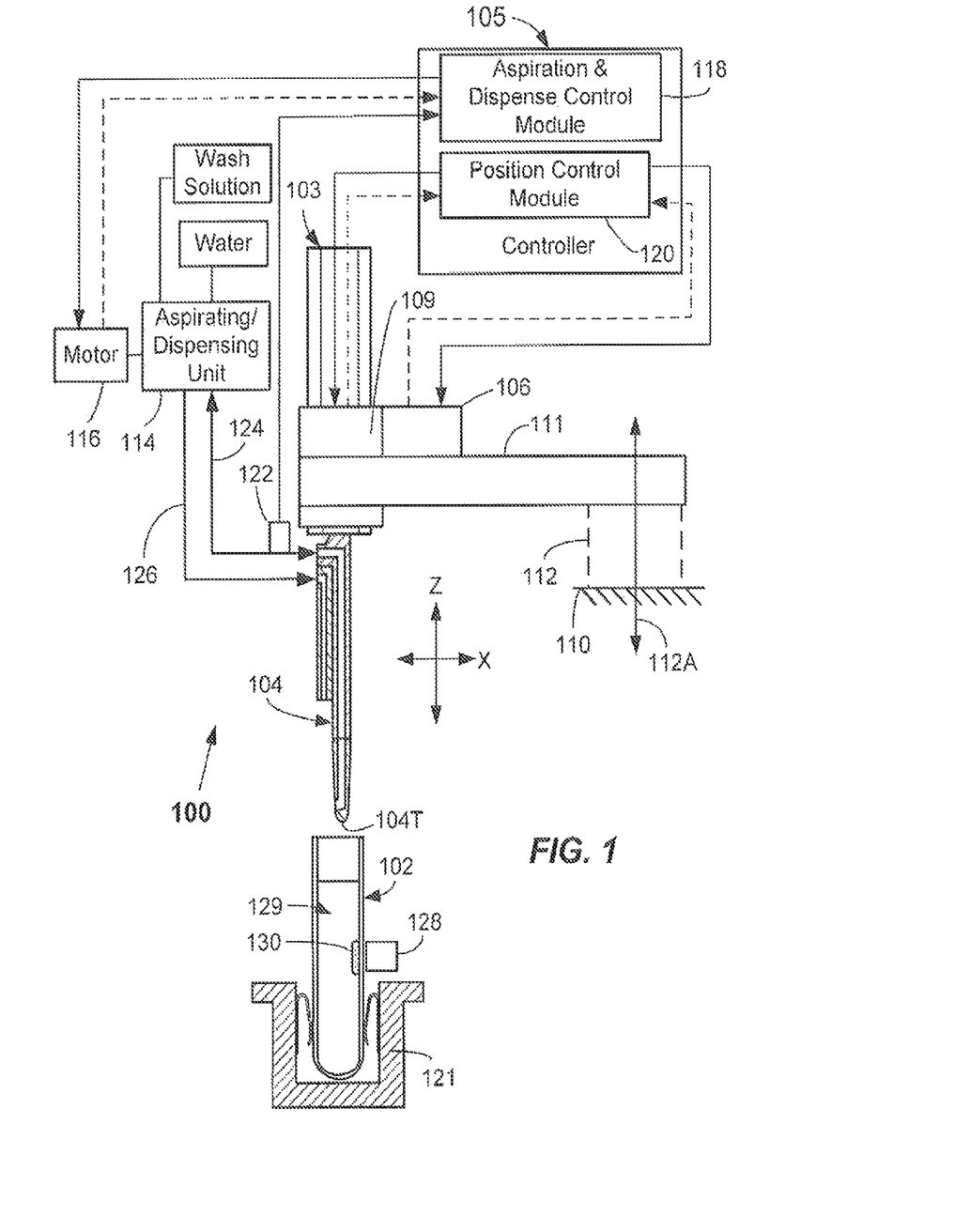
FIG. 1 illustrates a partially cross-sectioned side view of a magnetic particle washing apparatus according to embodiments.

An embodiment of a magnetic particle washing apparatus 100 that may be used with the present methods is best shown in FIG. 1. The magnetic particle washing apparatus 100 may be used for aspiration, transport, and dispensing of other liquids such as biological fluid, reagents, and the like, in addition to carrying out the washing method. Thus, the magnetic particle washing apparatus 100 may be configured and operational to carry out liquid transfer to and from a vessel 102 (e.g., a reaction cuvette). The magnetic particle washing apparatus 100, in some embodiments, is included in an automated clinical analyzer, or other processing or testing system (e.g., a biological fluid processing or testing system). In particular, the magnetic particle washing apparatus 100 is useful for precisely transferring a desired volume of a liquid and/or for carrying out magnetic particle washing methods in accordance with embodiments of the invention.

The various liquid(s) may be transferred from one location to another. For example, the magnetic particle washing apparatus 100 may be used to aspirate a precise volume of a biological liquid (e.g., blood, blood plasma, blood serum, interstitial fluid, urine, spinal fluids, or the like) and then dispense that liquid into the vessel 102 (e.g., the reaction vessel). Similarly, the magnetic particle washing apparatus 100 may be used to aspirate and dispense a precise volume of a reagent liquid. Such reagent liquid may be aspirated from a reagent-containing vessel (e.g., a Flex® reagent cartridge - not shown) and dispensed into the vessel 102. The magnetic particle washing apparatus 100 may be useful for transferring relatively small volumes of various liquids, such as between about 10 µL to about 150 µL. However, other liquid volumes may be transferred, as well. Liquids such as water or wash solution (collectively, or individually referred to herein as "wash liquid") may be dispensed and aspirated by the magnetic particle washing apparatus 100. Other liquids may be aspirated and/or dispensed as well.

The magnetic particle washing apparatus 100 may include a robot 103 having a probe 104 mechanically coupled thereto. The probe 104 may have a probe tip 104T having a hole adapted to aspirate or dispense liquid from an interior thereof. The probe 104 may be either directly connected to or interconnected to the robot 103. The probe 104 may be moveable in space by the robot 103. The magnetic particle washing apparatus 100 may include a suitable controller 105 that may command the robot 103, coupled probe 104, and, thus, probe tip 104T to move in space. For example, the robot 103 may move the probe tip 104T to and from one or more defined locations in space. In particular, the controller 105 may command the robot 103 to move in one or more coordinate directions (e.g., in an X, Y, or Z direction), two or more coordinate directions (e.g., X and Z, or Y and Z), three or more coordinate directions (e.g., X, Y, and Z, or X, R, and Z), where X is side-to-side motion along an X axis, Y is motion into and out of the paper in FIG. 1, R is rotational motion about an axis (e.g., axis 112A), and Z is vertical motion along a Z axis. The controller 105 may be any suitable electronic controller adapted to interact with the robot 103, and may include a suitable microprocessor, memory, power supply, conditioning electronics, one or more feedback sensors, and electronic circuitry adapted to carry out the one or more coordinate motions of the probe 104 and probe tip 104T.

In the depicted embodiment, any suitable robot 103 may be used. For example, a moveable multi-arm robot having one or more shoulder, elbow, and/or wrist elements may be used. Optionally, a telescopic boom robot may be used, where the probe 104 is coupled to the telescopic boom. In other embodiments, the robot 103 may have one or more moveable beams having one or more coupled motors, wherein the probe 104 is mechanically coupled to one of the beams or to a gantry arm. Thus, any suitable mechanism for imparting motion to the probe 104 may be used.

In one implementation, the robot 103 may be used to accomplish at least two-dimensional coordinate motion (e.g., X and Z) of the probe 104. In this manner, for example, the probe 104 may be moved in the X direction to a location above a first liquid-containing vessel (not shown) such as a reagent-containing vessel or biological fluid containing vessel. The probe 104 may then be lowered in the Z direction into the liquid (e.g., reagent liquid and/or biological fluid) contained in the vessel, and may aspirate a precise volume of the liquid into the probe 104. Additionally, the robot 103 may accomplish an upward retraction motion of the probe 104 in the Z direction and then motion in the X direction to a location above the vessel 102 (e.g., cuvette). The probe 104 may then be descended wherein the liquid may be dispensed into the vessel 102. The dispensing may typically involve lowering the probe 104 in the Z direction to a point in or just above the vessel 102 where the liquid is dispensed. Similarly, aspiration and dispensing of a biological fluid may occur, wherein the biological fluid and a reagent liquid may be mixed in the vessel 102. Magnetic particles may be added by various means, such as by dispensing a suspension of solid phase magnetic particles in liquid carrier or diluents. A reaction between the biological fluid and the reagent fluid may occur, and a high affinity surface on the magnetic particles may bind the chemical constituent or component of interest to the active surface thereof.

The robot 103 may, in order to impart motion to the probe 104, include one or more motion-producing components integral therewith or coupled thereto. For example, an X-axis motor 106 may be provided that is configured and operational to impart X-axis motion to the probe 104 relative to a frame 110 of the magnetic particle washing apparatus 100 fixed in space. A Z-axis motor 109 may be configured and operational to cause Z-axis motion of the probe 104 relative to the frame 110. In some embodiments, an additional drive motor 112 may impart a Y-axis motion of the robotic component 102 relative to the frame 110. In this configuration, X, Y, and Z axis motion of the probe 104 may be carried out. Optionally, the additional drive motor 112 may be a rotational motor imparting rotation of a beam 111 about the rotational axis 112A. Suitable feedback mechanisms may be provided for each degree of motion, such as by using position and/or rotation sensors or encoders. In the absence of the additional drive motor 112, the beam 111 may be directly attached to the frame 110 or otherwise rigidly connected to the frame 110. It should be recognized, however, that only z-axis motion may be used to carry out the magnetic particle washing methods according to some embodiments.

In the depicted embodiment, the robot 103 may include any suitable drive system including sprockets and chain, pulleys and belt, rack and pinion, gear or worm drive, or other conventional drive components. The motors 106, 109, 112 may be any suitable motor type, such as one or more stepper motors, servo motors, pneumatic or hydraulic motors, electric motors, linear motors, or combinations thereof.

Again referring to FIG. 1, the magnetic particle washing apparatus 100 may include an aspirating and dispensing unit 114. The aspirating and dispensing unit 114 may be fluidly connected to the probe 104 and operational to aspirate and/or dispense relatively accurate volumes of liquids, such as liquid reagent, biological fluid, saline buffer, and wash liquids such as water (e.g., purified water), and wash solution. Other liquids may be aspirated and/or dispensed, as well. The aspirating and dispensing unit 114 may include one or more suitable pumps that may be driven by one or more suitable motors 116, such as one or more stepper motors, for example. Other suitable motors may be used. The pumps may be any type of pumps suitable for dispensing relatively small liquid volumes, such as one or more piston pumps. Aspirating and dispensing unit 114 may be made up of multiple pumps adapted to dispense different volumes of fluid in some embodiments. Aspirating and dispensing unit 114 may include suitable conduits, valves and/or manifolds in order to aspirate and dispense the various liquids.

The aspirating and dispensing unit 114 may be driven/pumped in response to control signals from an aspiration and dispense control module 118 of the controller 105. Aspiration and dispense control module 118 may be a separate part of the controller 105 or integrated with the position control module 120. In one or mere embodiments, each module 118, 120 may include suitable control signal conditioning components such as filters, analog-to-digital converters, and/or amplifiers to send signals to the respective pump motors 116 and/or motors 106, 109, and/or 112 and receive feedback signals therefrom. Controller 105 may include a common microprocessor and memory for carrying out pre-programmed position and aspiration and dispense control instructions. Optionally, separate intercommunicating microprocessors and memories may be used to carry out position control and aspiration/dispense control.

The magnetic particle washing apparatus 100 may include a pressure sensor 122 fluidly coupled to the probe 104. For example, the pressure sensor 122 may be configured and functional and thus adapted to sense a representative aspiration pressure associated with the probe 104. The aspiration and dispense control module 118 may receive electronic signals (e.g., voltage signals) from the pressure sensor 122. The pressure sensor 122 may be configured and operational and thus adapted to measure and supply pressure readings associated with the aspiration by the probe 104. For example, the pressure sensor 122 may be coupled to the probe 104 or, as shown, coupled to a conduit 124 fluidly connecting the aspirating and dispensing unit 114 and the probe 104. These measured pressures may be used to verify proper aspiration. However, the volume aspirated or dispensed may be precisely controlled by the action of the pump motors 116 (e.g., by monitoring the turns of a stepper motor). The magnetic particle washing apparatus 100 may include a separate conduit 126 coupled to the aspirating and dispensing unit 114. Conduit 126 may be used to fill the vessel 102 with wash liquid at the start of each magnetic particle washing method according to embodiments. Optionally, fill may be through conduit 124.

As previously mentioned, the magnetic particle washing apparatus 100 may be adapted to transfer liquid (e.g., biological fluid sample and reagent) from one location to the vessel 102. The vessel may be received in a suitable holder 121 (e.g., a ring of a carousel) of the magnetic particle washing apparatus 100. After a reaction is carried out in the vessel 102 between the reagent and biological fluid and the analyte or constituent of interest is effectively bound to the magnetic particles, a magnetic field may be applied locally to the vessel 102 (e.g., to a side thereof) by a suitable magnetic field generating device 128, such as a magnet or electromagnet as shown in FIG. 1 to form a layer of magnetic particles 130. The layer of magnetic particles 130 may be quite small in comparison to the volume of the vessel 102. For example, the layer of magnetic particles may be less than 1 mm thick, and having a band height of about 3 mm, and a band width of about 10 mm, for example. The dimensions of the layer of magnetic particles 130 will largely be dictated by the magnetic field generator 128, for example. The layer of magnetic particles 130 may be generally centrally located along a length of the vessel 102. The magnetic particles may be coated, generally spherical magnetic particle beads of iron oxide. The magnetic particles may have a diameter of about 2.5 µm, for example. Other types of magnetic particles may be used.

Figure 2:
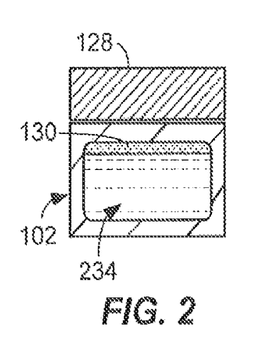
FIG. 2 illustrates a cross-sectioned top view of a vessel at a start of the magnetic particle washing method according to embodiments.

As shown in FIGS. 1 and 2, operation of the magnetic field generator 128 separates the magnetic particles from the remaining liquid 129, which may be a combination of reagent, biological fluid, and water, for example. This remaining liquid 129 may be aspirated and discarded (e.g., in a drain) such as by traversing the probe tip 104T to the bottom of the vessel 102 and then aspirating the remaining fluid 129, but leaving the layer of magnetic particles 130.

Figures 3, 5, 6:
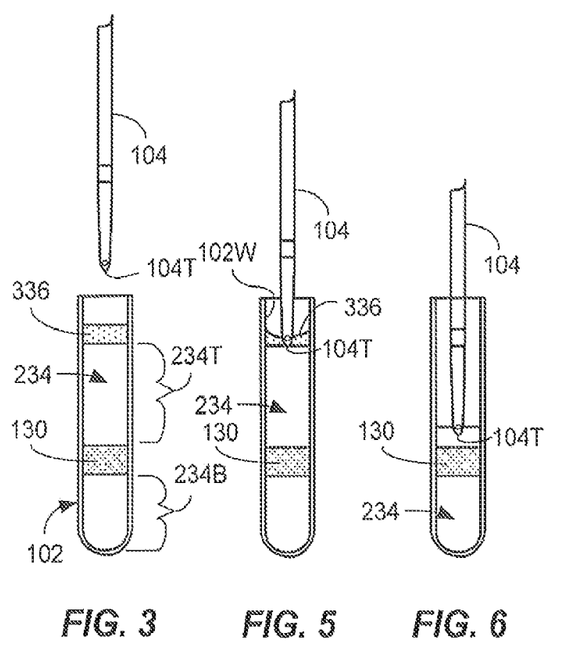
FIG. 3 illustrates a partially cross-sectioned side view of a vessel and probe at a start of the washing method according to embodiments.
FIG. 5 illustrates a partially cross-sectioned side view of a vessel and probe during a surface foam aspiration phase of the washing method according to embodiments.
FIG. 6 illustrates a partially cross-sectioned side view of a vessel and probe during a top wash liquid skimming phase of the washing method according to embodiments.

The method of washing the layer of magnetic particles 130 will now be described in detail with reference to FIGS. 1-9. As shown in FIG. 2, to start the washing method according to embodiments of the invention, the vessel 102 (e.g., held in holder 121), once the reaction liquids are aspirated and discarded, is provided and is filled with a suitable amount of a wash liquid 234, which may be a concentrated wash solution, water, or a combination thereof. The volume of wash liquid 234 introduced during each wash cycle may be between about 0.1 ml and 1 ml, for example. Other volumes greater than 1 ml may be used for larger vessels 102. The wash liquid 234 may be provided to a volume extent to fill the vessel 102 to a level above the location of the layer of magnetic particles 130, and in some embodiments, to about 0.2 cm above or greater, to above 1 cm or greater, or even to between about 0.2 cm to about 2 cm above a top of the layer of magnetic particles 130. In particular, as shown in FIG. 3, the amount of wash liquid 234 may be sufficient to form a top liquid portion 234T above the layer of magnetic particles 130, and a bottom liquid portion 234B below the layer of magnetic particles 130. The various steps in the washing method will be described herein. However, in some embodiments, the washing may be carried out more than once (e.g., repeated). Any suitable number of washing cycles may be carried out in sequence. For example, 1, 2, 3 or more washing cycles may be carried out for each layer of magnetic particles 130. If the vessel 102 resides in a holder 121, such as in a rotating carousel, then each successive wash cycle may take place at a different location and may therefore be accomplished with a different probe 104 and a different magnetic particle washing apparatus 100. For example, an analyzer may include 2 or more, 3 or more, or 4 or more such magnetic particle washing apparatus 100, and each wash cycle may be carried out at a different apparatus 100 after successive rotations of the carousel.

After removal of the contaminant liquids remaining after the reaction, the wash liquid 234 may be introduced by inserting the probe tip 104T to the bottom of the vessel 102 and filling the vessel 102 to the predefined depth. Thus, typically, at the start of the washing method, the vessel 102 may now include the wash liquid 234, and the layer of magnetic particles 130, which may be confined to a layer along the length of the vessel 102 and positioned on one side thereof. The magnetic field generator 128 remains positioned next to the side of the vessel 102 throughout the washing method thereby holding the layer of magnetic particles 130 against the sidewall of the vessel 102.

In some instances, such as shown in FIG. 3, surface foam 336 may be provided on the top surface of a meniscus of the wash liquid 234. According to the method, the probe tip 104T, exhibiting aspiration capability, may be descended from a position above the layer of magnetic particles 130 (e.g., from a home position as shown in FIG. 3) above the vessel 102. In some embodiments, the probe 104 may be descended with the suction as the probe tip 104T descends towards and through the top meniscus surface of the wash liquid 234. Optionally, the probe 104 may descend and the suction may be turned on at a position slightly above or below the top meniscus surface. As the probe tip 104T passes through the surface foam 336, at least some of the surface foam 336 present on the top meniscus may be aspirated. During the surface foam aspiration, the probe tip 104T may descend at a slow rate, such as less than about 3 cm/s with the suction on. The probe tip 104T may stop from time-to-time during the descent, such as while at the location of the top surface foam 336, or even below. During the aspiration of the top surface foam 336, the aspiration rate may be increased so as to effectively remove the top surface foam 336. As the probe tip 104T is further descended above the layer of magnetic particles 130, with the suction being on, aspiration of at least some of the top liquid portion 234T takes place. During the aspiration of the top liquid portion 234T, the probe tip 104T may remain very close to the top meniscus surface during a substantial portion of the aspirating. This is referred to as the "skimming phase" of the washing process wherein the top liquid portion 234T is aspirated.

Figure 4:
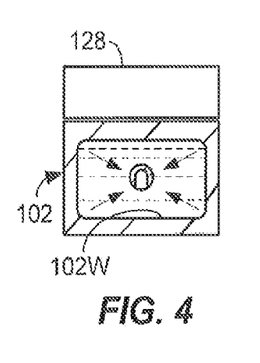
FIG. 4 illustrates a cross-sectioned top view of a vessel and probe during the magnetic particle washing method according to embodiments.

During the skimming phase, the probe tip 104T may be positioned by the controller 105 at less than about 1.5 mm from the meniscus surface of the wash liquid 234, less than about 1 mm from the meniscus surface of the wash liquid 234, or even less than 0.5 mm from the meniscus surface of the wash liquid 234, or even slightly above the meniscus surface in some embodiments. The probe tip 104T may descend at a desired rate by the position control 120 as the skimming phase takes place with the probe tip 104T positioned close to the top meniscus of the wash liquid 234 during a substantial portion of the aspirating. The descent may be continuous or interspersed with stops followed by further incremental descents during the skimming phase. In some embodiments, the probe tip 104T is maintained at less than about 1.5 mm from the meniscus surface of the wash liquid 234 during at least 50%, at least 75%, or even substantially all of the volume aspiration of the top liquid portion 234T. Keeping the probe tip 104T relatively close to the top meniscus surface of the wash liquid 234 during the skimming phase of the washing method produces an effect such as shown in FIG. 4, wherein the top surface foam 336 and wash liquid 234 is readily drawn away from the walls 102W of the vessel 102 and removed as shown in FIGS. 5 and 6.

During the skimming phase, the top surface foam 336 (if present), and top liquid portion 234T may be aspirated and quite effectively removed as the suction is applied. The descent rate during the skimming phase may be less than about 5 cm/sec, less than about 3 cm/sec, and between about 1 cm/sec and about 5 cm/sec in some embodiments. The goal is descend with suction applied at a sufficiently slow rate so that the tip 104T remains relatively close to the meniscus so that the pattern represented by the arrows in FIG. 4 may be established, drawing the wash liquid 234 and any top surface foam 336 away from the walls 102W (in the direction of arrows) which may effectively minimizing droplet adherence thereto. To achieve the skimming effect while aspirating, a descent rate and a volume aspiration rate may be selected such that the probe tip 104T may be maintained at a position of less than about 1.5 mm from a top meniscus of the wash liquid 234, or even closer. Once the descent rate is selected, a suitable aspiration rate may be selected based upon the relative size of the vessel 102 to keep the probe tip 104T near the top meniscus surface. Smaller vessels may require smaller descent rates and/or smaller aspiration rates.

The descent and the skimming phase of the washing process may continue suctioning off at least a portion of the top liquid portion 234T until the probe tip 104T reaches a predetermined depth, which may be at a location somewhat above of the layer of magnetic particles 130 as shown in FIG. 6. At this location, the suction may be turned off via action of the aspiration and dispense control module 118 turning off the aspirating and dispensing unit 114. For example, this location for turning off the suction may be greater that about 0.1 cm above the top of the layer of magnetic particles 130, or between about 0.1 cm and about 0.7 cm above the top of the layer of magnetic particles 130 in some embodiments. Other values may be used.

Figure 7:
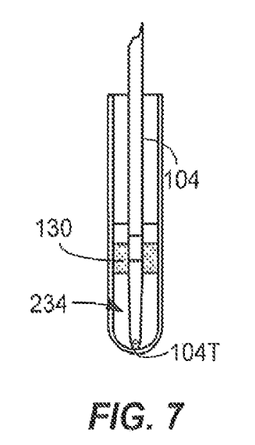
FIG. 7 illustrates a partially cross-sectioned side view of a vessel and probe during a probe descending phase of the washing method according to embodiments.
Figure 8:
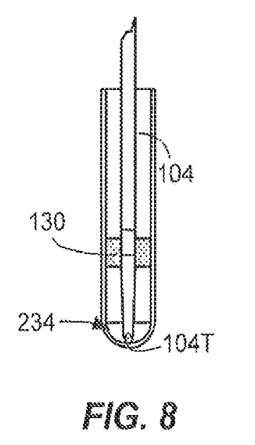
FIG. 8 illustrates a partially cross-sectioned side view of a vessel and probe during a bottom wash liquid aspiration phase of the washing method according to embodiments.

Next, the probe tip 104T is positioned below the layer of magnetic particles 130 by descending the probe tip 104T under the control of the position control module 120. During the descent, the probe tip 104T traverses past the layer of magnetic particles 130 with the suction to the probe 104 turned off. The probe tip 104T is further descended to position below the layer of magnetic particles 130 where the probe tip 104T may be positioned within about 10 mm from a bottom of the vessel 102, for example. In other embodiments, a location for turning on the suction may be greater that about 0.3 cm below a bottom of the layer of magnetic particles 130, or between about 0.3 cm and 2 cm below the bottom of the layer of magnetic particles 130. Keeping a distance away from the layer of magnetic particles 130 may prevent magnetic particles from being aspirated. At this location, the suction may again be turned back on wherein at least some of the bottom liquid portion 234B of the wash liquid 234 is aspirated. In one or more embodiments, the probe tip 104T may be provided in contact with a bottom of the vessel 102, such as shown in FIG. 7.

During the descent below the layer of magnetic particles 130, a descent rate of the probe tip 104T may be about 1.5 times greater than, or even 2 times greater, or even 20 times greater than the descent during the skimming phase. In some embodiments, the descent rate may be greater than about 5 cm/s, and between about 5 cm/s and about 40 cm/s in some embodiments. Other descent rates may be used. During the aspiration below the layer of magnetic particles 130, at least some of the wash liquid 234 from below the layer of magnetic particles 130 is aspirated. This aspiration of the bottom liquid portion 234B below the layer of magnetic particles 130 may be carried out at a volume aspiration rate of greater than about 2.5 cm$^3$/s, or even between about 2.5 cm$^3$/s and about 5 cm$^3$/s in some embodiments. Other aspiration rates may be used. During the bottom liquid portion aspiration phase, the aspiration may continue until the wash liquid 234 is substantially removed. Again, if the initial washing method is insufficient to adequately wash the layer of magnetic particles 130, the vessel 102 may be refilled with wash liquid 234 to a level above the layer of the magnetic particles 130 and the wash method may be repeated.

Figure 9:
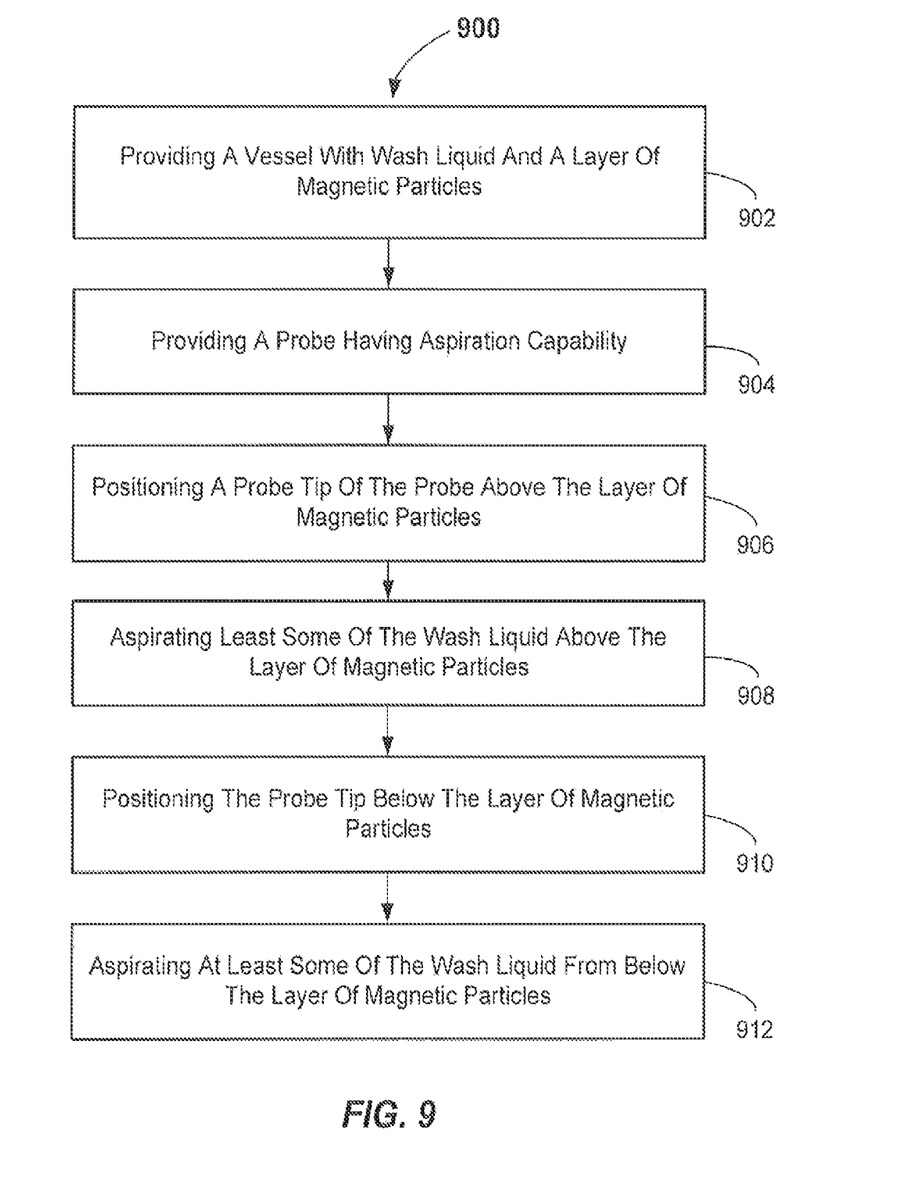
FIG. 9 is a flowchart illustrating a method of washing magnetic particles according to embodiments.

The method 900 of washing the magnetic particles according to embodiments of the invention will now be explained in detail with reference to the flowchart shown in FIG. 9, the magnetic particle washing apparatus 100 shown in FIG. 1, and the various side views in FIGS. 3-8. The method 900 includes, in 902, providing a vessel (e.g., 102) with wash liquid (e.g., 234) and a layer of magnetic particles (e.g., 130), and, in 904, providing a probe (e.g., 104) having aspiration capability. In 906, a probe tip (e.g., 104T) of the probe is positioned above the layer of magnetic particles (e.g., under the action of the controller 105), and in 908, at least some of the wash liquid above the layer of magnetic particles (e.g., top liquid portion 234T) is aspirated (e.g., under the action of the aspirating and dispensing unit 114). During the aspirating of at least some of the wash liquid from above the layer of magnetic particles, the probe tip may be descending while aspirating with a descent rate and a volume aspiration rate selected such that the probe tip is maintained at a position of less than about 1.5 mm from a top meniscus of the wash liquid.

In 910, the probe tip is positioned below the layer of magnetic particles (e.g., by robot 103 and controller 105), and in 912, at least some of the wash liquid from below the layer of magnetic particles (e.g., bottom liquid portion 234B) is aspirated (e.g., by aspirating and dispensing unit 114). As the probe tip is descended past the layer of magnetic particles the suction to the probe may be turned off.

While the invention is susceptible to various modifications and alternative forms, specific system embodiments and methods thereof have been shown by way of example in the drawings and are described in detail herein. It should be understood, however, that it is not intended to limit the invention to the particular systems or methods disclosed but, to the contrary, the intention is to cover all modifications, equivalents, and alternatives falling within the scope of the invention.

What is claimed is:

1. A method of washing magnetic particles, comprising:
   providing a vessel with wash liquid and a layer of magnetic particles;
   providing a probe having aspiration capability;
   positioning a probe tip of the probe above the layer of magnetic particles;
   aspirating at least some of the wash liquid above the layer of magnetic particles;
   passing the probe tip past the layer of magnetic particles with suction to the probe turned off;
   positioning the probe tip below the layer of magnetic particles; and
   aspirating at least some of the wash liquid from below the layer of magnetic particles.

2. The method of washing of claim 1, wherein the positioning of the probe tip above the layer of magnetic particles comprises initially descending the probe tip with suction on until at least some of any top surface foam present on a top meniscus of the wash liquid is aspirated.

3. The method of washing of claim 2, comprising slowly descending the probe in the top surface foam present on a top meniscus at a descent rate of less than about 3 cm/s.

4. The method of washing of claim 1, wherein the positioning of the probe tip above the layer of magnetic particles comprises slowly descending the probe tip in the wash liquid at a descent rate of less than about 5 cm/s.

5. The method of claim 4, comprising a descent rate of between about 1 cm/s and about 5 cm/s.

6. The method of claim 1, wherein the aspirating of at least some of the wash liquid above the layer of magnetic particles comprises aspirating the wash liquid at a volume aspiration rate of between about 0.5 cm$^3$/s and about 3 cm$^3$/s.

7. The method of claim 1, wherein the aspirating of at least some of the wash liquid above the layer of magnetic particles comprises descending the probe tip while aspirating with a descent rate and a volume aspiration rate selected such that the probe tip is maintained at a position of less than about 1.5 mm from a top meniscus of the wash liquid.

8. The method of claim 1, wherein the aspirating of at least some of the wash liquid above the layer of magnetic particles comprises descending the probe tip while aspirating at a descent rate of between about 1 cm/s and about 5 cm/s and a volume aspiration rate of between about 0.5 cm$^3$/s and about 3 cm$^3$/s selected such that the probe tip is maintained at a position within about 0.5 mm and about 1.5 mm from a top meniscus of the wash liquid.

9. The method of claim 1, wherein the positioning of the probe tip below the layer of magnetic particles comprises positioning the probe tip within about 10 mm from a bottom of the vessel.

10. The method of claim 1, wherein the positioning of the probe tip below the layer of magnetic particles comprises contacting the probe tip with a bottom of the vessel.

11. The method of claim 1, wherein the positioning of the probe tip below the layer of magnetic particles comprises descending the probe tip at a descent rate below the layer of magnetic particles of greater than about 5 cm/s.

12. The method of claim 11, wherein the descent rate comprises between about 5 cm/s and about 40 cm/s.

13. The method of claim 1, wherein the aspirating of at least some of the wash liquid from below the layer of magnetic particles comprises aspirating the wash liquid below the layer of magnetic particles at a volume aspiration rate of between about 2.5 $cm^3$/s and about 5 $cm^3$/s.

* * * * *